(12) United States Patent
Chen

(10) Patent No.: US 7,276,143 B2
(45) Date of Patent: Oct. 2, 2007

(54) ELECTROPHORESIS MODULE HAVING ELECTROPHORESIS BATH WITH UPRIGHT CARRIERS

(76) Inventor: Hui-Wan Chen, 27Fl, No. 29-1, Sec. 2, Jungieng E. Road, Dan Shuei Jen, Taipei County 251 (TW)

( * ) Notice: Subject to any disclaimer, the term of this patent is extended or adjusted under 35 U.S.C. 154(b) by 759 days.

(21) Appl. No.: 10/713,015

(22) Filed: Nov. 17, 2003

(65) Prior Publication Data

US 2005/0103632 A1    May 19, 2005

(51) Int. Cl.
*G01N 27/453* (2006.01)
(52) U.S. Cl. .................................. 204/618; 204/467
(58) Field of Classification Search ........ 204/456–470, 204/606–610, 612–620, 600
See application file for complete search history.

(56) References Cited

U.S. PATENT DOCUMENTS

| | | | | |
|---|---|---|---|---|
| 3,932,265 A | * | 1/1976 | Hoefer | 204/619 |
| 4,325,796 A | * | 4/1982 | Hoefer et al. | 204/467 |
| 5,112,470 A | * | 5/1992 | Sylvester | 204/618 |
| 5,632,877 A | * | 5/1997 | Van Atta | 204/618 |
| 5,882,495 A | * | 3/1999 | Garrels | 204/456 |
| 5,888,364 A | * | 3/1999 | Schuette | 204/466 |
| 6,110,340 A | * | 8/2000 | Lau et al. | 204/467 |
| 6,193,868 B1 | * | 2/2001 | Hsu | 204/618 |
| 6,942,775 B1 | * | 9/2005 | Fox | 204/467 |
| 2005/0103628 A1 | * | 5/2005 | Jackson et al. | 204/456 |

* cited by examiner

*Primary Examiner*—Kaj K. Olsen
(74) *Attorney, Agent, or Firm*—Bacon & Thomas, PLLC

(57) ABSTRACT

The electrophoresis module has an upright cassette of which at least one of the front and rear sides has a recess opened upwardly, the recess has on the peripheral edge thereof a buffering member; the cassette has on the two ends thereof a clamping assembly each, each clamping assembly is composed of a front and a rear clip and a rotating knob in order that a set of carrier can be placed in the recess of the cassette and between the clips, and the rotating knob is rotated to make the clips press the carrier toward the buffering member on the peripheral edge of the recess; then gel pouring and sealing operation is performed after sealing the periphery of the carrier set, and lastly, the cassette clamping the carrier set is placed in the electrophoresis bath for directly proceeding with electrophoresis separation engineering.

9 Claims, 12 Drawing Sheets

ELECTROPHORESIS MODULE HAVING ELECTROPHORESIS BATH WITH UPRIGHT CARRIERS

BACKGROUND OF THE INVENTION

1. Field of the Invention

The present invention is related to an electrophoresis module having an electrophoresis bath with upright carriers, and especially to such a module of biotechnology which uses electrophoresis to proceed with analysis engineering of DNA (deoxyribonucleic acid), RNA (ribonucleic acid) and protein, in which sets of carriers poured with gel and sealed are conveniently placed in the electrophoresis bath for proceeding with an electrophoresis separation engineering.

2. Description of the Prior Art

Electrophoresis was designed for separation and analysis of DNA (deoxyribonucleic acid), RNA (ribonucleic acid) and protein in biotechnology; its principle is using electric current to drive molecules to render the molecules drift on gel of porous substance, in movement, the molecules are separated by difference in amount and size of the electric charges and the ionic ingredients thereof, this owns an extremely important position in application of the basic theory of biotechnology.

As shown in FIG. 1, before performing of a separation engineering, the sample solution and gel to be separated and analyzed shall be poured in a gap in a set of carrier 30; the carrier set 30 has two thin sheets 31 made of glass or acryl provided peripherally with pads 32 of suitable thickness, and then have the thin sheets 31 clamped with clips 60, a gap is formed between the two thin sheets 31, due to the thickness of the separating pads 32, the abovementioned sample solution and gel to are poured in the gap in the carrier set 30. When the gel coagulates and is shaped, the carrier set 30 poured with gel and sealed can be placed in the electrophoresis bath for proceeding with electrophoresis separation engineering.

A conventional clip 60 for clamping the carrier set 30 only has a clamping action rather than effective positioning for the carrier set 30, the two thin sheets 31 are subjected to being displaced, or the entire set of carrier 30 are subjected to collision to affect the effect of the gel manufactured during pouring with gel and sealing or during placing in the electrophoresis bath after coagulating of the gel. Particularly, the carrier set 30 must even be more carefully placed on a receiving member to wait for setting and shaping of the gel. Thereby the process of production of the entire sample is complicated, and is subjected to damaging the equipment or the sample.

For getting rid of the defect that the normal clips are unable to surely position a set of carrier 30, as is shown in FIG. 2, some use a frame 70 to directly press two thin sheets 31 by means of adjusting screws 71, this can make positioning of the carrier 30 as well as avoid collision. However, by virtue that each set of carrier 30 shall be pressed for fixing by more than four adjusting screws 71, it is unable to fast and accurately adjust the depth of pressing of the adjusting screws 71, and the gap between the two thin sheets 31 is unable to be uniform; particularly when the adjusting screws 71 are rotated with an overly large force, the two thin sheets 31 can be damaged.

Additionally, a conventional electrophoresis separator principally renders an electrophoresis bath to proceed with separation and analysis, the carrier sets on the two kind of carrier set clamping structures stated above shall still be moved into the electrophoresis bath after being taken out of the receiving member when manufacturing of the samples are completed; the carrier sets are positioned through frequent fixing actions. In this view, the separator is still not so convenient in use as expected, and even the accuracy of molecular maps may be affected by frequent errors of actions.

SUMMARY OF THE INVENTION

The present invention has an upright cassette of which at least one of the front and rear sides has a recess opened upwardly, the recess has on the peripheral edge thereof a buffering member; the cassette has on the two ends thereof a clamping assembly each, each clamping assembly is composed of a front and a rear clip and a rotating knob in order that a set of carrier can be placed in the recess of the cassette and between the clips, and the rotating knob is rotated to make the clips press the carrier toward the buffering member on the peripheral edge of the recess; then gel pouring and sealing operation is performed after sealing the periphery of the carrier set, and lastly, the cassette clamping the carrier set is placed in the electrophoresis bath for directly proceeding with electrophoresis separation engineering.

The present invention will be apparent in its structural assembling and the entire mode of operation after reading the detailed description of the preferred embodiment thereof in reference to the accompanying drawings.

DETAILED DESCRIPTION OF THE PREFERRED EMBODIMENT

Figure 1:
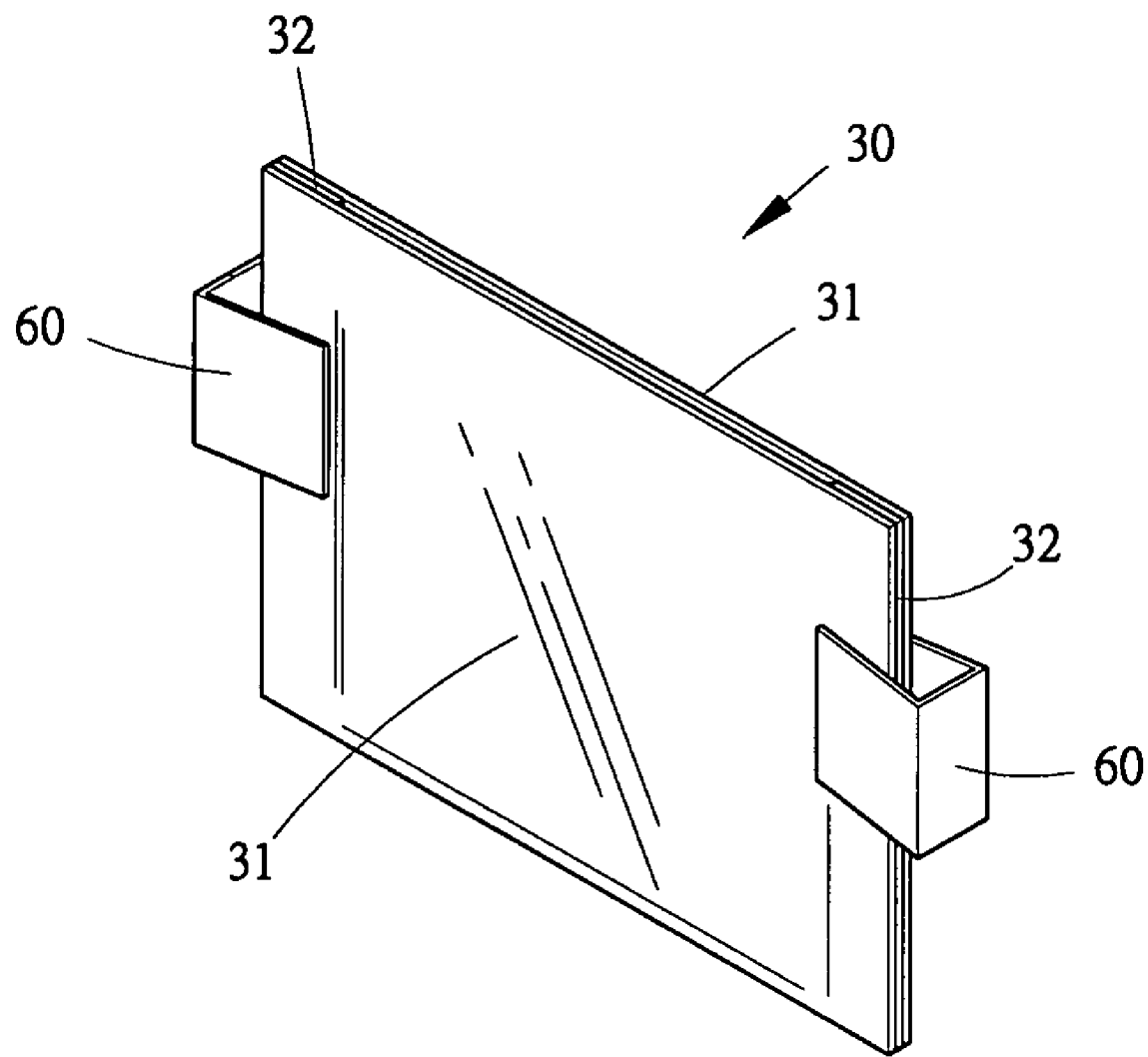
FIG. 1 is a perspective schematic view showing conventional clips for fixing thin sheets.
Figure 2:
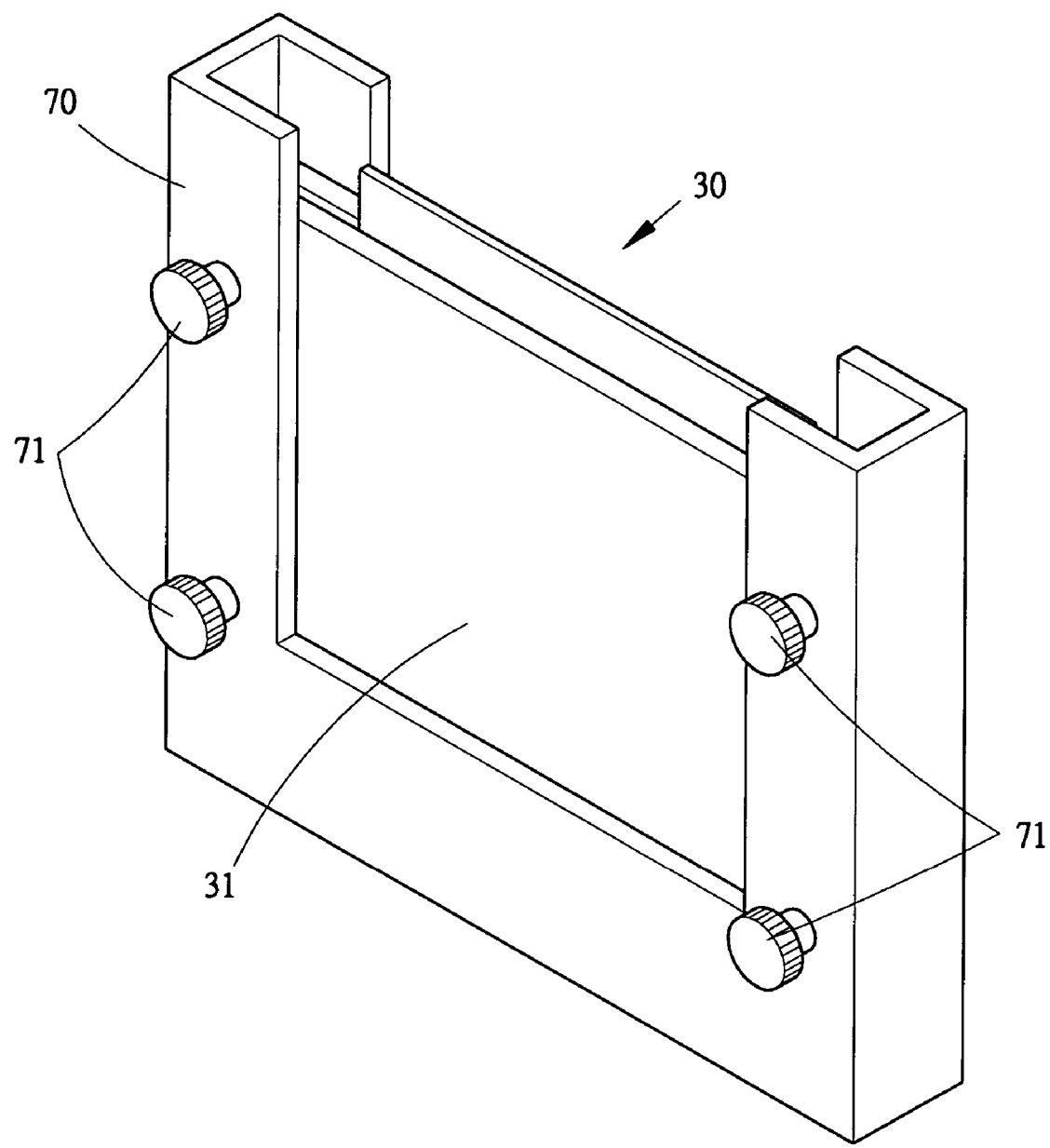
FIG. 2 is a perspective schematic view showing a conventional way of fixing thin sheets using screws.
Figure 3:
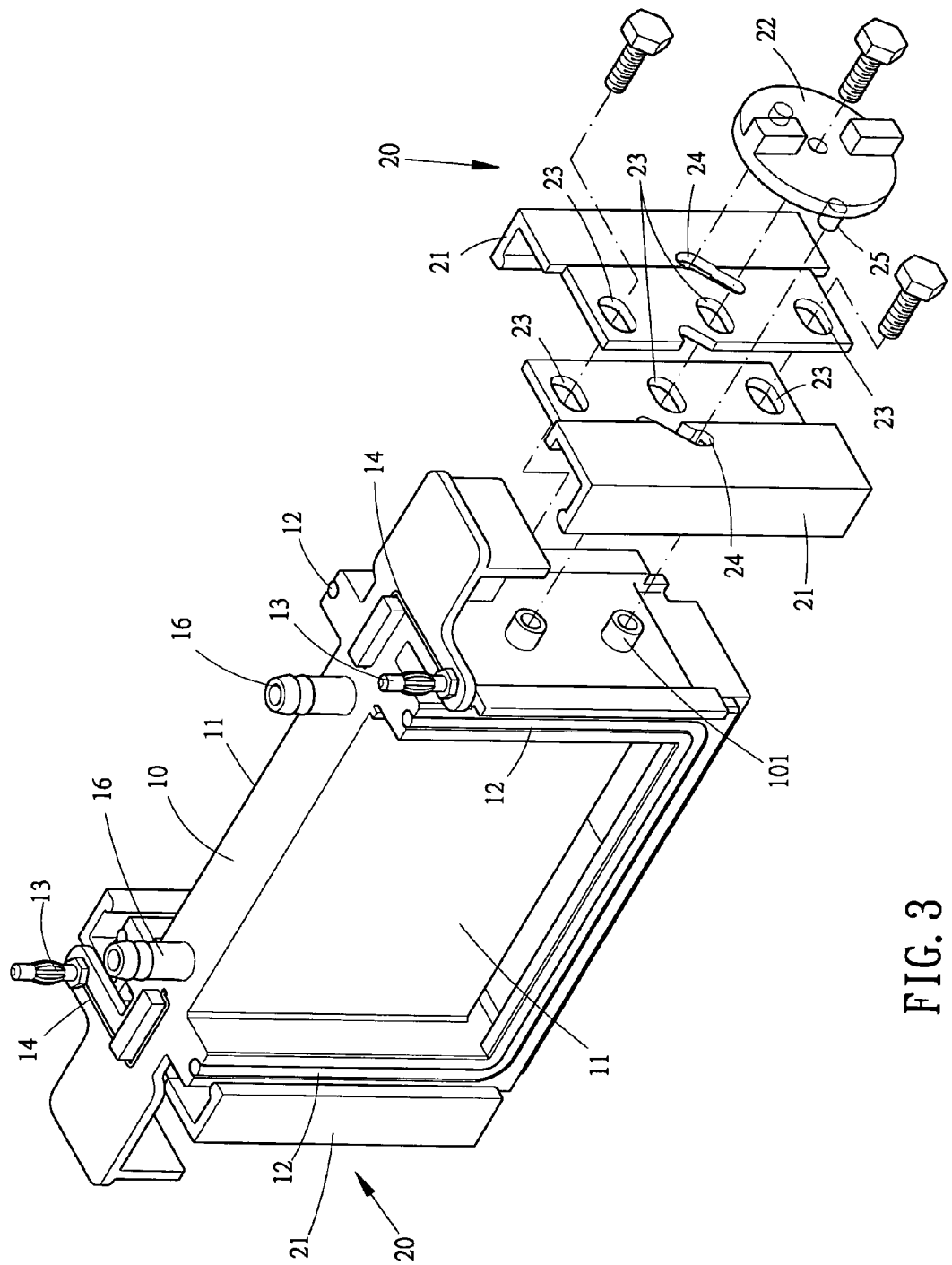
FIG. 3 is an analytic structural perspective view of an electrophoresis module of the present invention.
Figure 4:
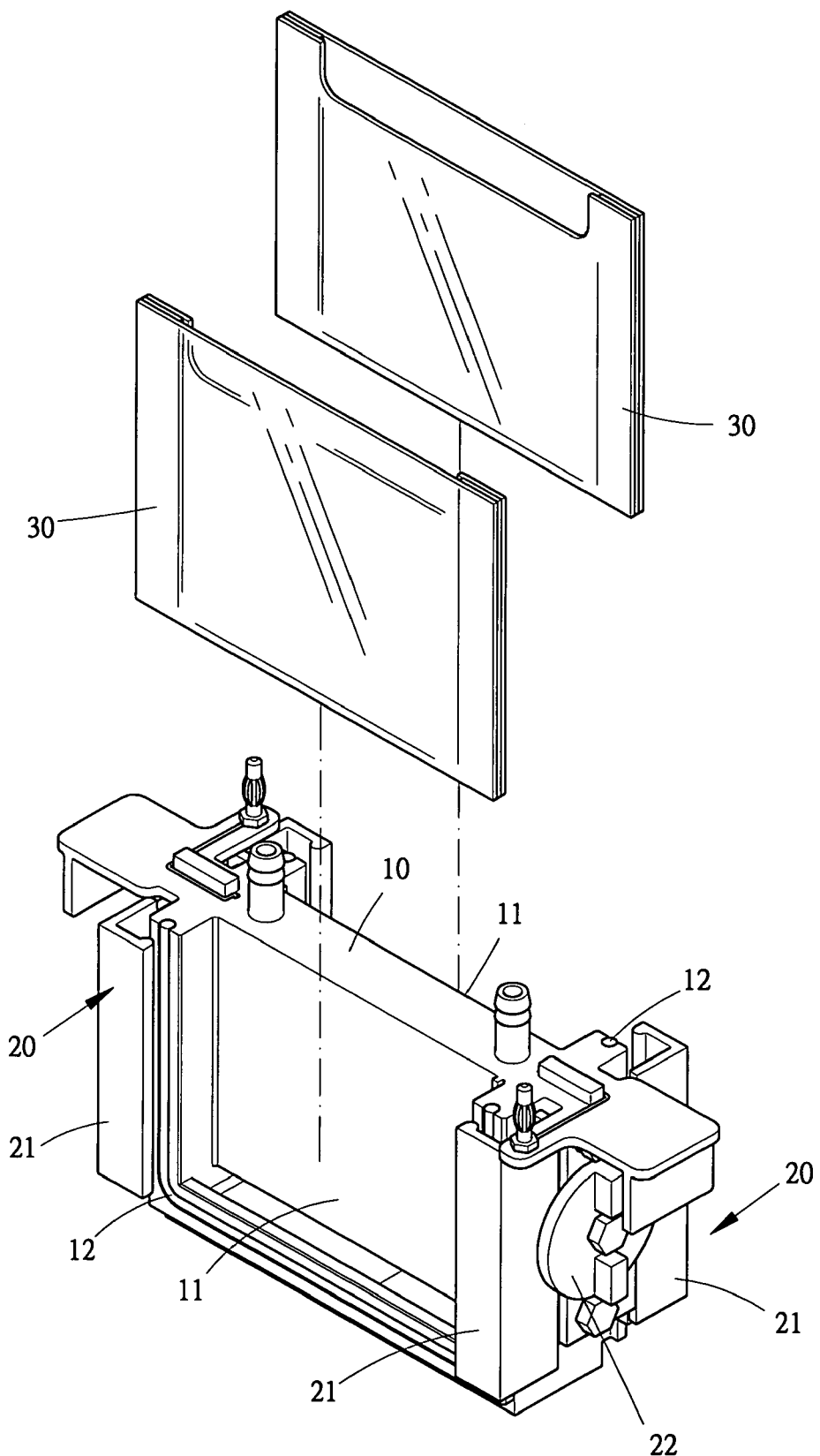
FIG. 4 is a perspective schematic view showing the mode of mounting carrier sets of the present invention.

The "electrophoresis module having an electrophoresis bath with upright carriers" of the present invention provides an electrophoresis module that can accurately clamp and fix carrier sets and can be directly placed in an electrophoresis bath when in an electrophoresis engineering, as are shown in FIGS. 3 and 4. The entire electrophoresis module has an upright cassette 10 of which at least one of the front and rear sides has a recess 11 opened upwardly, the recess 11 has on the peripheral edge thereof a buffering member 12; while in the embodiment as shown in the drawings, the cassette 10 has a recess 11 and a buffering member 12 both on the front and rear sides thereof, the buffering member 12 can be made from a rubber strip.

And the cassette 10 has on the right and left ends thereof a clamping assembly 20 each, each clamping assembly 20 is composed of a front and a rear clip 21 and a rotating knob 22 for moving the two clips 21. Taking the front side of the cassette 10 as an example, a set of carrier 30 can be placed in the recess 11 on the front side of the cassette 10 and between the front clips 21 at the two ends of the cassette 10. And the rotating knobs 22 at the right and left ends are rotated to make the front clips 21 move and press tightly the carrier set 30 on the buffering member 12 on the peripheral edge of the recess 11, thereby to fast and accurately clamp and fix the carrier set 30. The carrier set 30 has two thin sheets made of glass or acryl provided peripherally with pads of suitable thickness, and then has the thin sheets clamped with clips, the thickness of the separating pads forms a gap between the two thin sheets, sample solution and gel are then poured in the gap between the two thin sheets to proceed with a gel pouring and sealing operation; this is a conventional technique, and will be not narrated further more.

Figure 5:
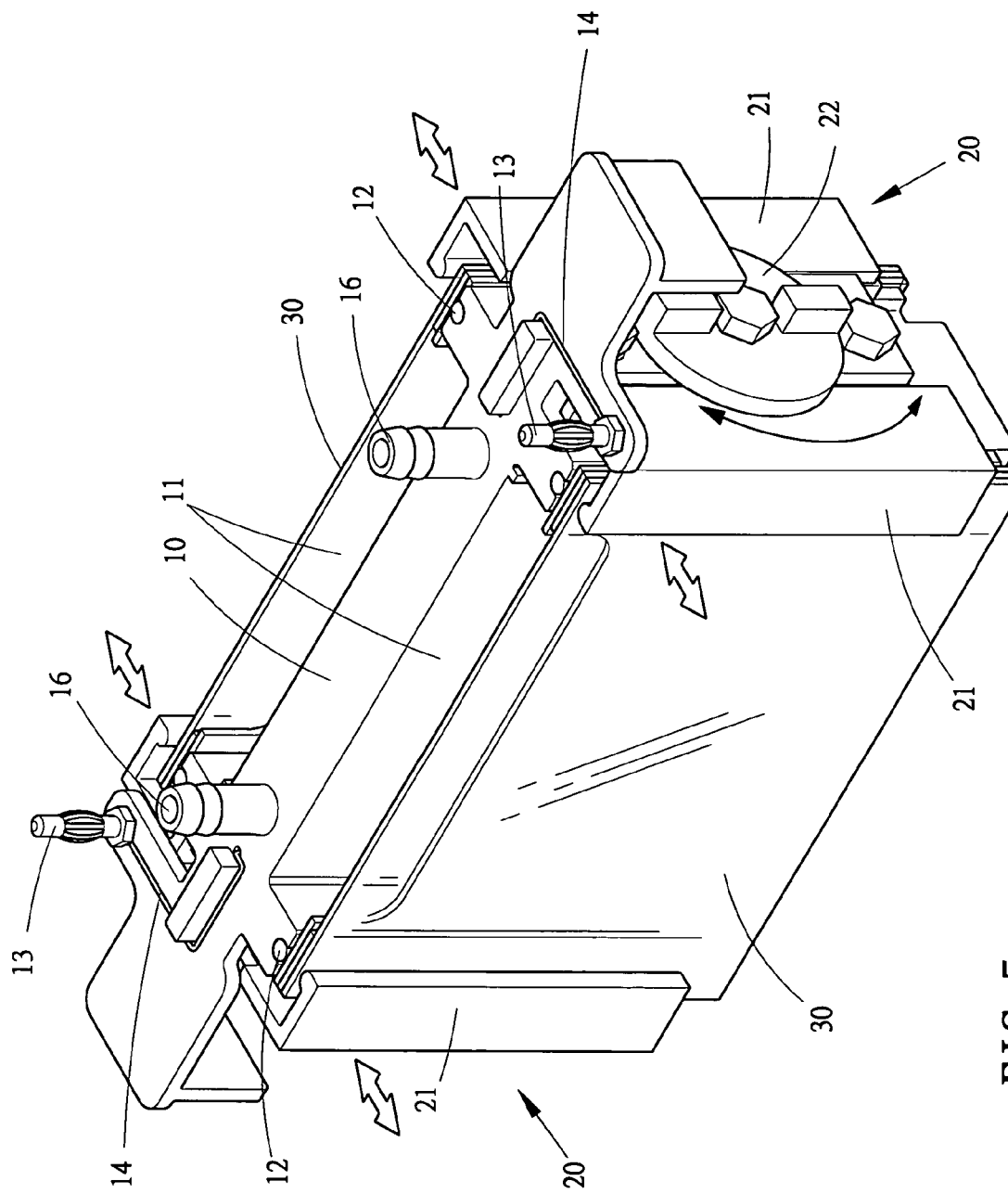
FIG. 5 is a perspective schematic view showing the state of clamping carrier sets of the electrophoresis module of the present invention.

Referring to FIG. 5 simultaneously, the aforesaid cassette 10 has on the right and left ends thereof a clamping assembly 20 each; taking a clamping assembly 20 as an example, the front and the rear clips 21 are same but direct to mutual contrary directions. And further taking the front clips 21 as an example, each of the front clips 21 has a plurality of guide slots 23 facing in the direction parallel to that of clamping of the carrier set 30 and has a bevel slit 24; wherein the cassette 10 has a plurality of protrusions 101 in corresponding with the guide slots 23 to allow the protrusions 101 to slip in the slots 23; the rotating knobs 22 have pusher rods 25 insertable into the bevel slits 24, when in rotating the rotating knobs 22, the pusher rods 25 inserted into the bevel slits 24 can displace in the bevel slits 24 and push the front clips 21 rearwards, meantime move the front clips 21 rearwards synchronically by guiding of the guide slots 23 of the protrusions 101, and press the carrier set 30 toward the rear recess 11, thereby the carrier set 30 is pressed tight and fixed. In this way, a simple action of rotating the rotating knobs 22, the carrier set 30 can be fixed by clamping to effectively prevent movement of the carrier set 30. When it is to take out the carrier set 30, the front clips 21 can be released by rotating the rotating knobs 22 in contrary directions.

As stated before, the front and the rear clips 21 of each clamping assembly 20 are same structurally but direct to mutual contrary directions, they can clamp another carrier set 30, and no further description is required here for it. The function of a buffering member 12 is to prevent displacement of a carrier set 30 when some clips 21 press the carrier set 30, or to prevent breaking of a carrier set 30 when an action force is too large.

Figure 6:
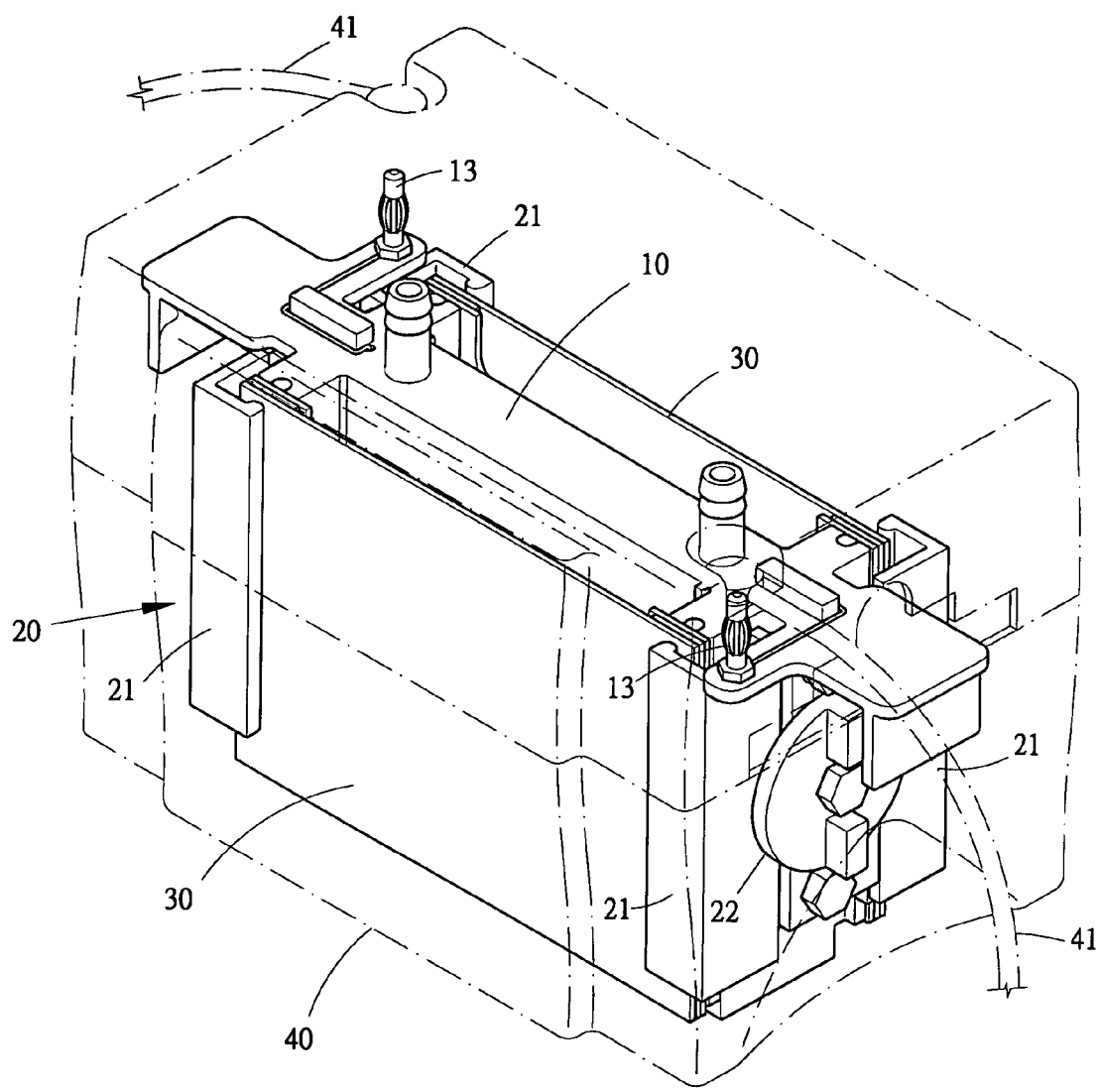
FIG. 6 is a perspective schematic view showing the state of use of the electrophoresis module of the present invention.

And more, the top of the cassette 10 has on each end thereof a connecting electrode 13; the two connecting electrodes 13 have between them conductors 14 extending to the bottom of the cassette 10. And therefore as shown in FIG. 6, carrier sets 30 poured and sealed therein with sample solution and gel can be placed in an electrophoresis bath 40, they can be connected with a power line 41 by means of the two connecting electrodes 13 on the top of the cassette 10. Connection with the electric source is done after buffering liquid is poured into the electrophoresis bath 40, and then the electrophoresis separation engineering for separation and analysis of DNA (deoxyribonucleic acid), RNA (ribonucleic acid) and protein can be directly proceeded with. This can save the frequent actions of fixing the carrier sets 30 to make the process of the entire electrophoresis separation engineering more simplified to thereby effectively maintain the accuracy of the electrophoresis separation engineering.

Figure 7:
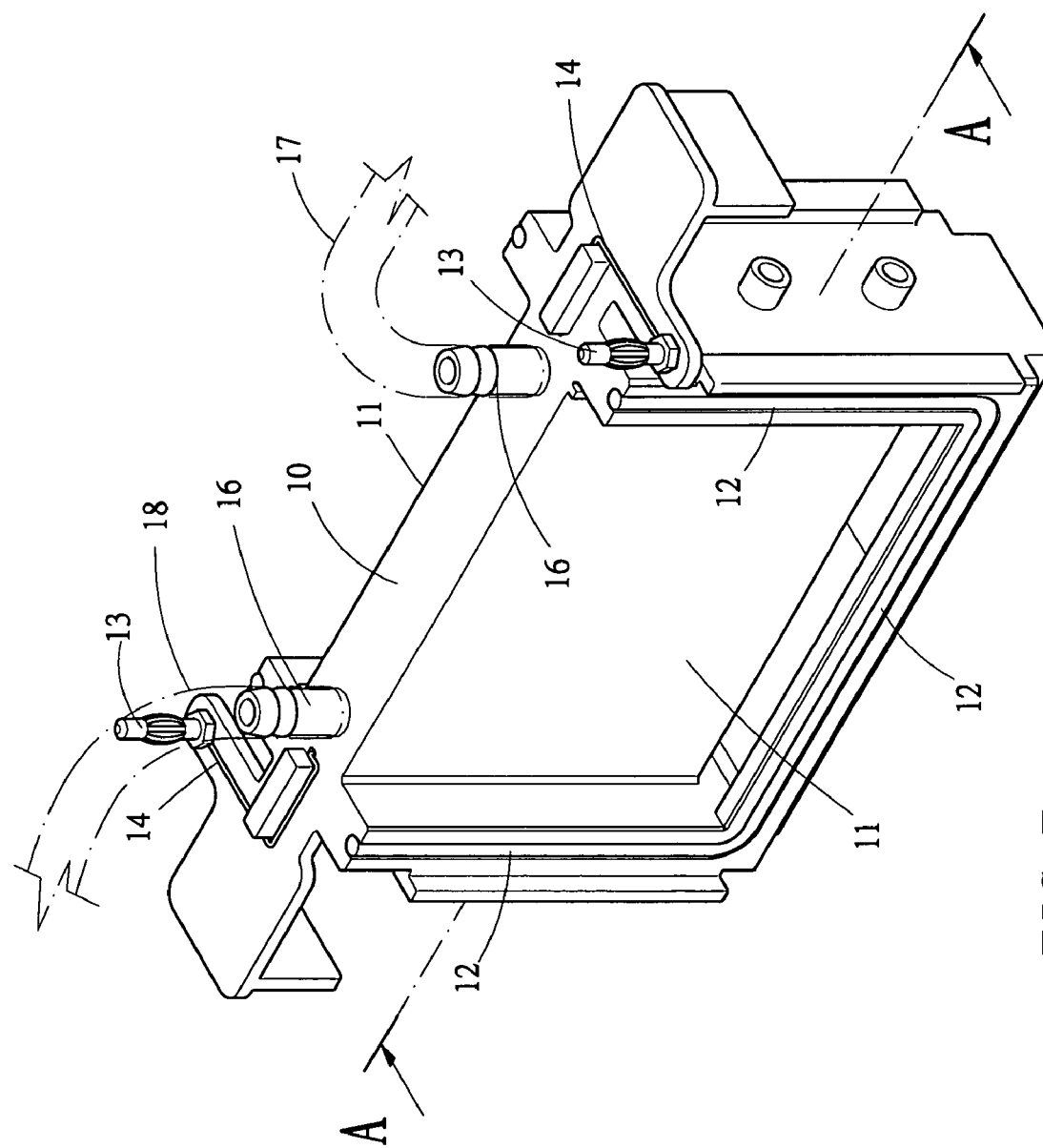
FIG. 7 is a perspective view showing the appearance structurally of a cassette of the present invention.
Figure 8:
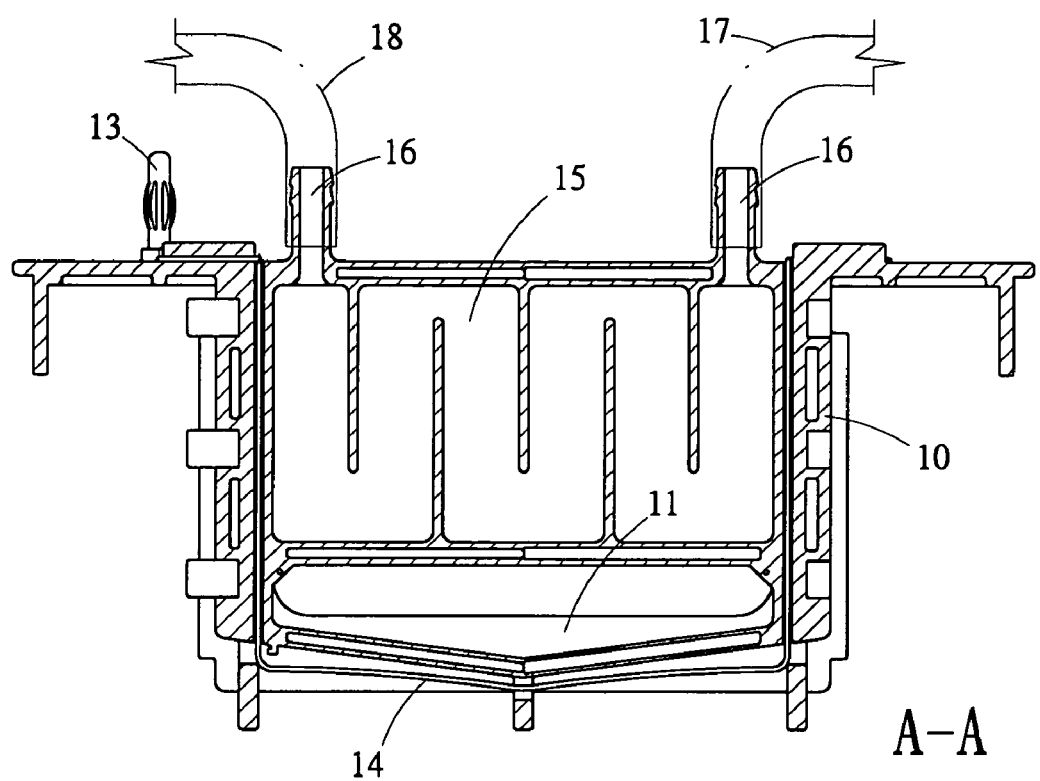
FIG. 8 is a sectional view showing the structure of the cassette of the present invention.

By the fact that the cassette 10 is a member which is placed in the electrophoresis bath 40 together with the carrier sets 30 to execute the electrophoresis engineering, as are shown in FIGS. 7 and 8, the cassette 10 can be provided therein with a tortuous passage 15, the two ends of the tortuous passage 15 are provided with connecting pipes 16 to connect respectively with a water inlet 17 and a water outlet 18, so that cooling water can get in and out of the cassette 10 to cool the working temperature of an electric conducting device in the electrophoresis bath 40. And each recess 11 of the cassette 10 has on the bottom thereof a construction that has the two lateral sides thereof tilted down toward the middle area, the inclined surfaces can thus create an action to accelerate raising of bubbles in order to prevent breaking of electric conduction by the bubbles generated by electric connecting of the buffering liquid, and thereby to effectively control proceeding of the electrophoresis engineering.

Figure 9:
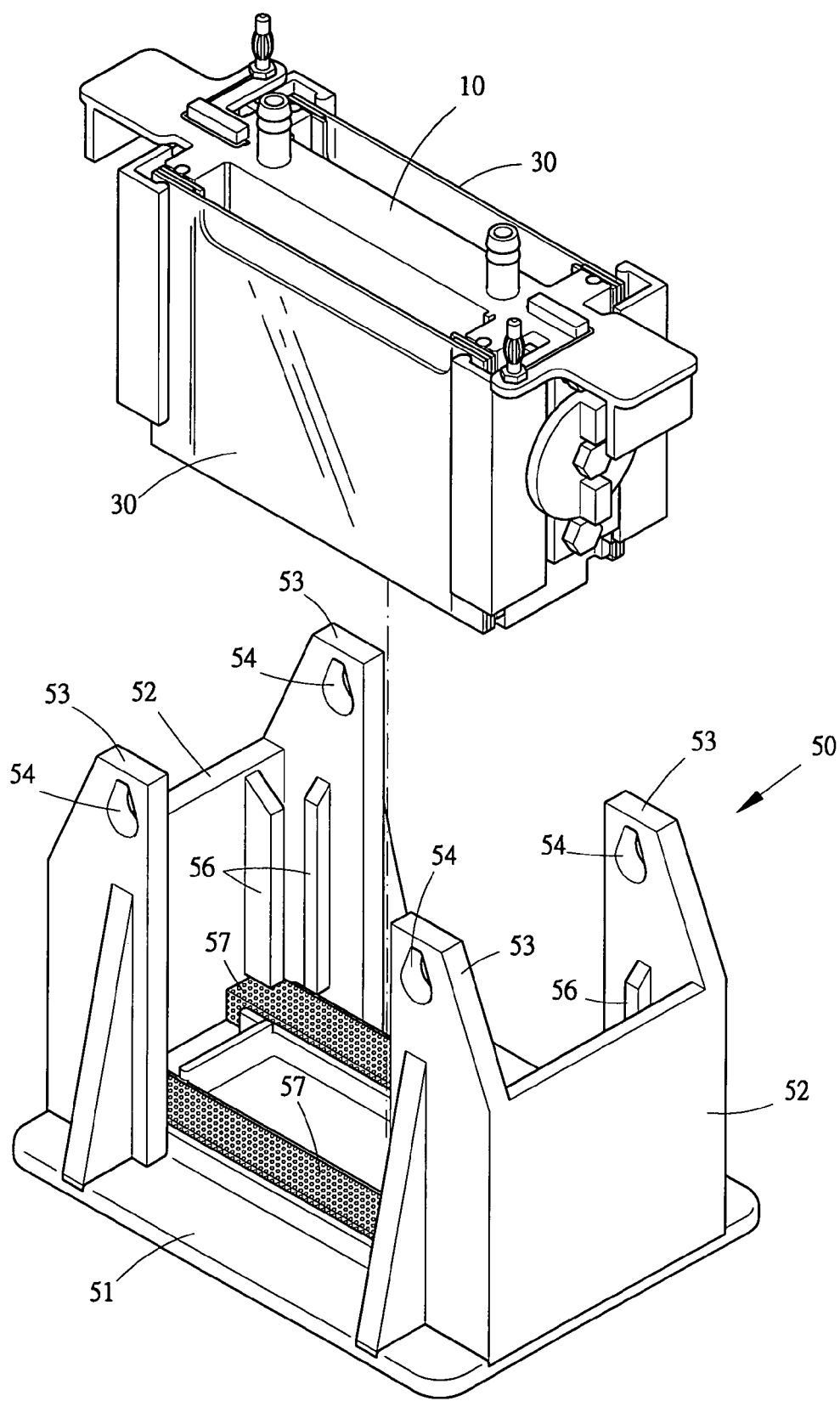
FIG. 9 is a perspective schematic view showing the appearance structurally of a rack of the present invention.
Figure 10:
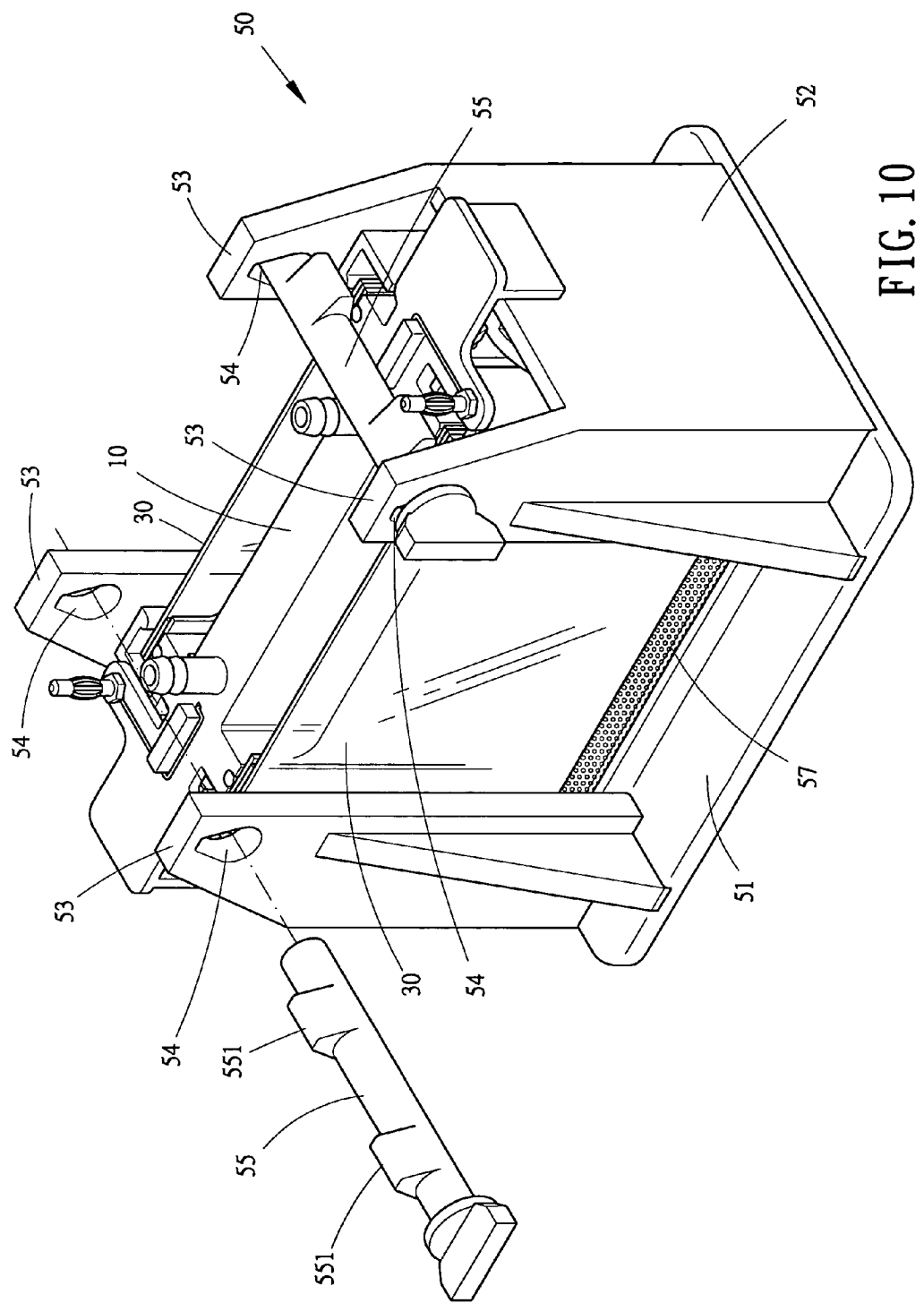
FIG. 10 is a perspective schematic view showing the mode of mounting cam axles on the rack of the present invention.

And further as shown in FIGS. 9 and 10, the entire electrophoresis module of the present invention can be provided with a rack 50 for alignment of the tops of the carrier sets 30, and for placing therein the members including the cassette 10 and the carrier sets 30 etc. for storage when the cassette 10 is not in use. Wherein the rack 50 has a bottom board 51 for placing the cassette 10, the bottom board 51 is provided thereon with upright walls 52 to frame correspondingly the cassette 10; the upright walls 52 each has on the inner wall thereof positioning strips 56 for guiding positioning of the cassette 10, the bottom board 51 further has two protruding portions 53 being on the areas corresponding with the two lateral side parts of the cassette 10 and extending over the top of the cassette 10, The protruding portions 53 has axle holes 54 in favor of extending of a cam axle 55 between the two axle holes 54 of the two mutually opposite protruding portions 53; the cam axle 55 has cams 551 to contact the tops of the carrier sets 30; and the bottom board 51 has elastic pads 57 at the locations corresponding with the bottom edges of the carrier sets 30.

Figure 11:
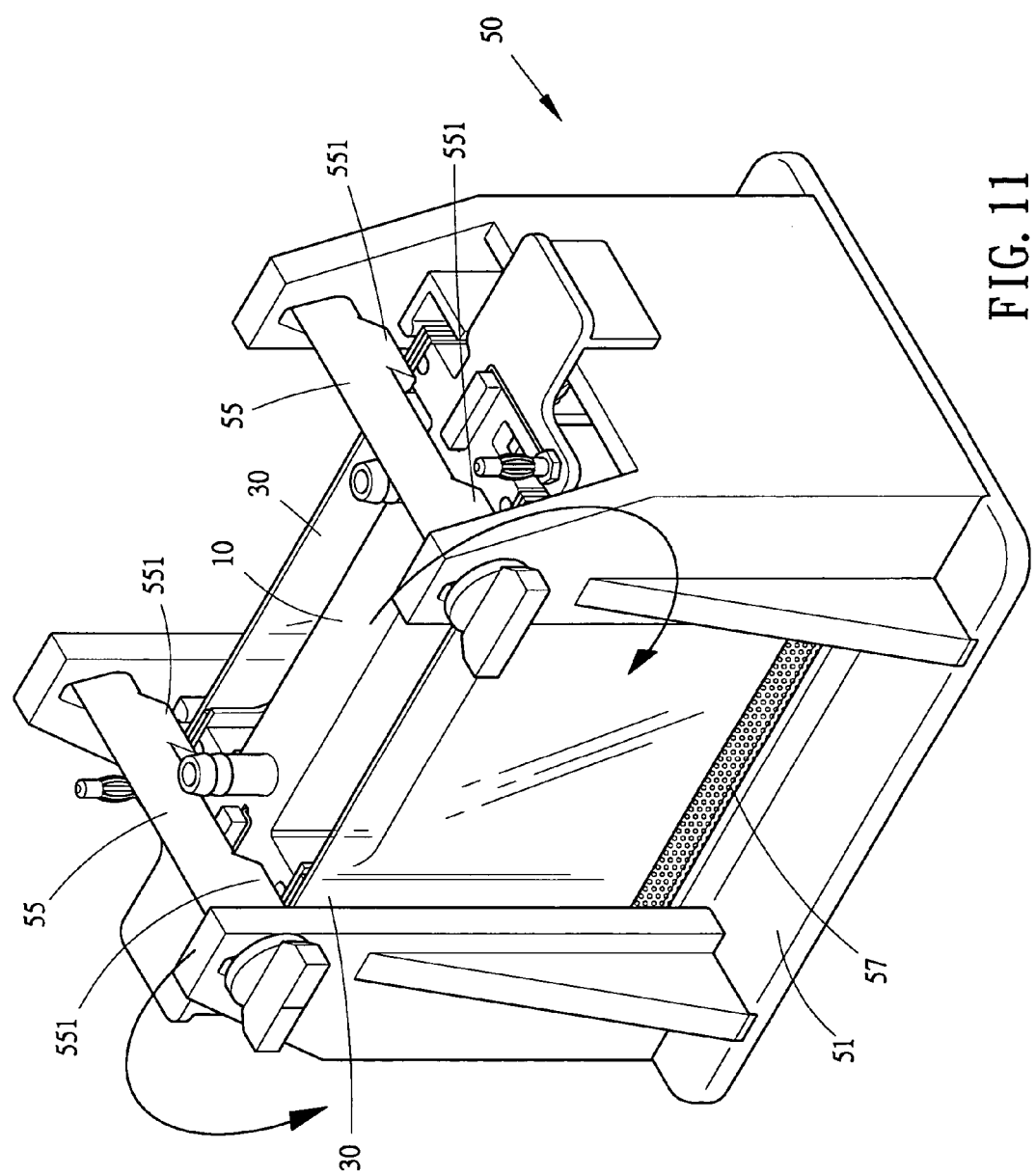
FIG. 11 is a perspective schematic view showing the state of aligning the top edges of the carrier sets by means of the rack of the present invention.

Therefore, when the carrier sets 30 are clamped on the cassette 10, the cassette 10 can be placed in the rack 50 together with the carrier sets 30, such as is shown in FIG. 10. And the cam axle 55 then is extended between the two axle holes 54 of the rack 50 and on the tops of the cassette 10. Further as shown in FIG. 11, rotating the cam axle 55 can make the cams 551 press the tops of the carrier sets 30, and press the carrier sets 30 toward the bottom board 51. At this time, the elastic pads 57 at the bottom board 51 will have elastic deformation by pressing of the carrier sets 30, and form an upwardly pushing action against the carrier sets 30 in contrary directions, so that the bottoms of the carrier sets 30 are sealed; and the carrier sets 30 are flush with the top of the cassette 10 because the tops of them are impeded by the cams 551 in order that the pouring and sealing operation of the sample solution and gel can be performed before the carrier sets 30 are placed into the electrophoresis bath, and thereby a molecular map acquired in the subsequent electrophoresis engineering can be more accurate.

Figure 12:
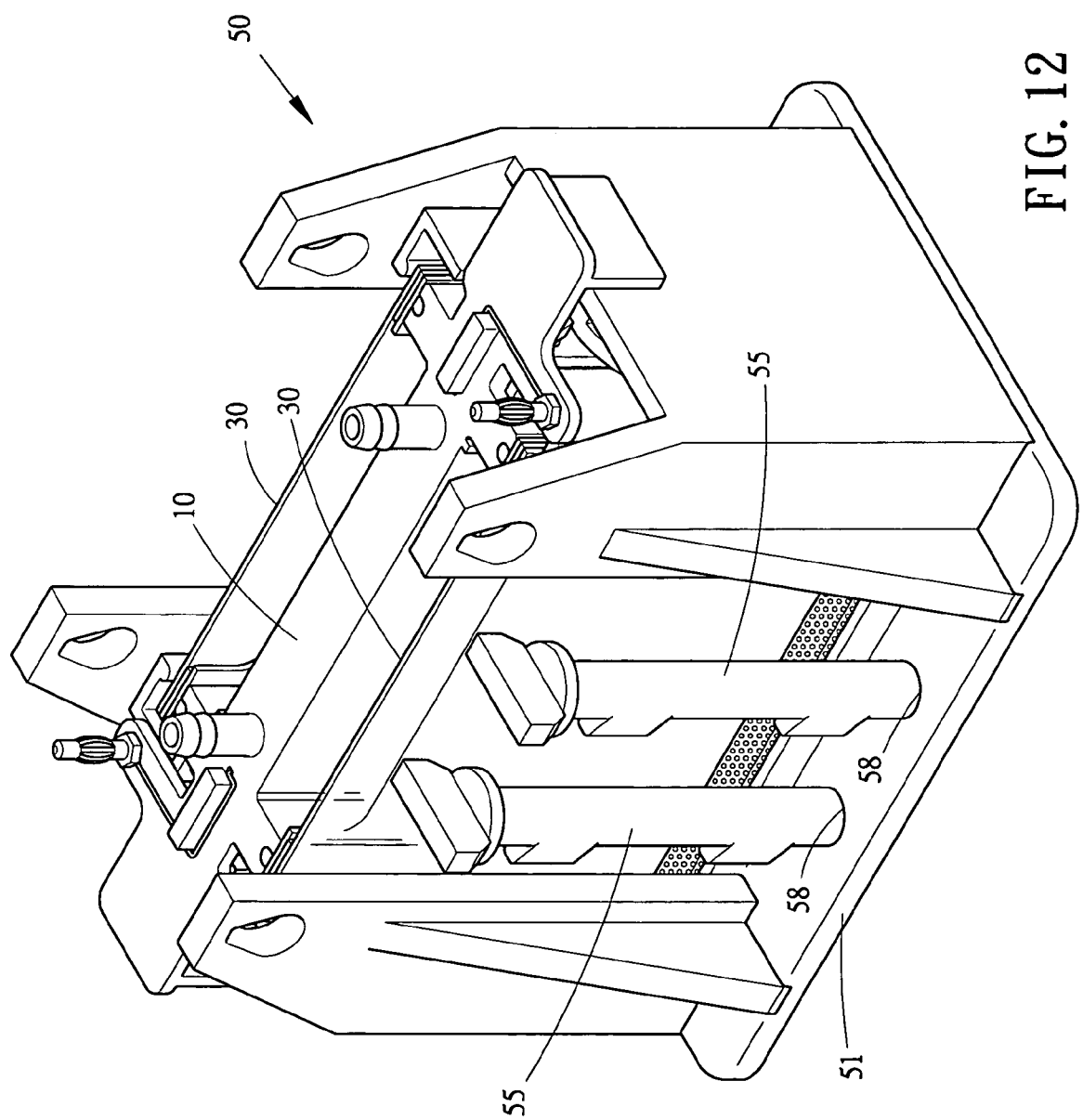
FIG. 12 is a perspective schematic view showing the state of centralized preservation of the members including the cassette, the carrier sets and the cam rods etc. by means of the rack of the present invention.

Moreover, when not in executing the electrophoresis engineering, as is shown in FIG. 12, the rack 50 can also be used for placing the cassette 10 and the carrier sets 30 to make centralized preservation of the latter for preventing losing or unnecessary collision; surely the bottom board 51 of the rack 50 can also be provided with holes 58 for insertion of the cam axles 55 for the axle holes on the two ends of the rack 50, so that the cam axles 55 can also be preserved in the mode of centralization.

The specification and the drawings are only for illustrating a preferred embodiment of the present invention, and not for giving any limitation to the scope of the present invention. It will be apparent to those skilled in this art that various equivalent modifications or changes without departing from the spirit of this invention shall also fall within the scope of the appended claims.

The invention claimed is:

1. An electrophoresis module having an electrophoresis bath with upright carriers, said module has an upright cassette provided on a right and a left end thereof with a clamping assembly each; said clamping assembly is composed of at least a clip and a rotating knob for moving said clip; wherein said clip has a plurality of guide slots facing in a direction parallel to that of clamping of sets of said carriers for slipping of a plurality of protrusions provided correspondingly on said cassette in said guide slots, and has a bevel slit linked with said rotating knob, said rotating knob has a pusher rod insertable into said bevel slit, when in rotating said rotating knob, said pusher rod and said bevel slit push and guide to press said carrier sets toward said cassette.

2. The electrophoresis module having an electrophoresis bath with upright carriers as in claim 1, wherein: said clamping assembly has said clip both at a front and a rear side of said cassette.

3. The electrophoresis module having an electrophoresis bath with upright carriers as in claim 2, wherein: said cassette has a recess opened upwardly both on said front and rear sides thereof, said recess has on a peripheral edge thereof a buffering member.

4. The electrophoresis module having an electrophoresis bath with upright carriers as in claim 1, wherein: a top of said cassette has on each end thereof a connecting electrode; said connecting electrodes have between them conductors extending to a bottom of said cassette, said cassette clamping therein said carrier sets is placed in an electrophoresis bath, said connecting electrodes on said top of said cassette are connected with a power line to proceed with an electrophoresis separation engineering.

5. The electrophoresis module having an electrophoresis bath with upright carriers as in claim 1, wherein: said cassette is provided therein with a tortuous passage, two ends of said tortuous passage are provided with connecting pipes to connect respectively with a water inlet and a water outlet, so that cooling water gets in and out of said cassette to cool working temperature of an electric conducting device in said electrophoresis bath.

6. The electrophoresis module having an electrophoresis bath with upright carriers as in claim 1, wherein: said cassette has on a bottom thereof a construction that has two lateral sides thereof tilted down toward a middle area thereof, this creates an action to accelerate raising of bubbles in order to prevent said bubbles generated by electric connecting of a kind of buffering liquid from attaching to surfaces of said cassette or said carrier sets.

7. The electrophoresis module having an electrophoresis bath with upright barriers as in claim 1, wherein: said electrophoresis module is provided with a rack, said rack has a bottom board for placing said cassette, said bottom board is provided thereon with upright walls to frame correspondingly said cassette; said bottom board further has protruding portions being on areas corresponding with two lateral side parts of said cassette and extending over a top of said cassette, said protruding portions have axle holes in favor of extending of cam axles between said axle holes of every two mutually opposite ones of said protruding portions; said cam axles each has cams to contact tops of said carrier sets; and said bottom board has elastic pads at locations corresponding with bottom edges of said carrier sets; when said carrier sets are clamped on said cassette, said cassette is placed in said rack together with said carrier sets, and said cam axles then are extended between corresponding ones of said axle holes of said rack and on said tops of said cassette; rotating said cam axles makes said cams press said tops of said carrier sets, and said cassette is entirely pressed together with said carrier sets toward said elastic pads to have said bottom edges of said carrier sets sealed by pushing action of said elastic pads, and said carrier sets are flush with said top of said cassette in order that pouring and sealing operation of sample solution and gel is performed.

8. The electrophoresis module having an electrophoresis bath with upright carriers as in claim 7, wherein: said bottom board of said rack is provided with holes for insertion of said cam axles.

9. The electrophoresis module having an electrophoresis bath with upright carriers as in claim 7, wherein: said upright walls of said rack is provided on an inner wall thereof with positioning strips for guiding positioning of said cassette.

* * * * *